United States Patent
Ichikawa et al.

(10) Patent No.: US 11,690,942 B2
(45) Date of Patent: Jul. 4, 2023

(54) BLOOD PURIFICATION APPARATUS WITH A BYPASS LINE THAT BYPASSES AN ULTRAFILTRATION PUMP

(71) Applicant: Nikkiso Company Limited, Tokyo (JP)

(72) Inventors: Takeshi Ichikawa, Shizuoka (JP); Satoshi Takeuchi, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 1011 days.

(21) Appl. No.: 16/296,679

(22) Filed: Mar. 8, 2019

(65) Prior Publication Data

US 2019/0201609 A1 Jul. 4, 2019

Related U.S. Application Data

(63) Continuation of application No. PCT/JP2017/032778, filed on Sep. 12, 2017.

(30) Foreign Application Priority Data

Sep. 12, 2016 (JP) .............................. JP2016-177939

(51) Int. Cl.
*A61M 1/34* (2006.01)
*A61M 1/36* (2006.01)
*A61M 1/16* (2006.01)

(52) U.S. Cl.
CPC ............ *A61M 1/3424* (2014.02); *A61M 1/16* (2013.01); *A61M 1/165* (2014.02);
(Continued)

(58) Field of Classification Search
CPC ........ A61M 1/14; A61M 1/16; A61M 1/1629; A61M 1/165; A61M 1/34; A61M 1/3417;
(Continued)

(56) References Cited

U.S. PATENT DOCUMENTS

| 4,493,693 A | 1/1985 | Bilstad et al. |
| 5,336,051 A | 8/1994 | Tamari |

(Continued)

FOREIGN PATENT DOCUMENTS

| CN | 102958547 A | 3/2013 |
| EP | 0330891 A1 | 9/1989 |

(Continued)

OTHER PUBLICATIONS

JP5356853B2 Furuhashi et al.—Blood Purification Apparatus (Abstracts. MT; Aug. 26, 2010; 43 pages) (Year: 2010).*

(Continued)

*Primary Examiner* — Hayden Brewster
(74) *Attorney, Agent, or Firm* — Young Basile Hanlon & MacFarlane, P.C.

(57) ABSTRACT

A blood purification apparatus that is capable of, with no preparatory operations, performing substitution by supplying dialysate in a dialysate introduction line to a blood circuit during ultrafiltration treatment, or performing blood return by immediately supplying the dialysate in the dialysate introduction line to the blood circuit after the ultrafiltration treatment. A blood purification apparatus includes a dialyzer, a dialysate introduction line, a dialysate drain line L2 through which drain liquid from the dialyzer is drained, and an ultrafiltration pump capable of removing water from the blood in the blood circuit. The blood purification apparatus is capable of performing substitution or blood return by supplying the dialysate in the dialysate introduction line L1 to the blood circuit. In an ultrafiltration treatment in which the ultrafiltration pump is activated while the introduction of the dialysate into the dialyzer is stopped, dialysate delivery is performed while the introduction of the dialysate into the dialyzer is prevented.

19 Claims, 7 Drawing Sheets

(52) U.S. Cl.
CPC ............ *A61M 1/1629* (2014.02); *A61M 1/34* (2013.01); *A61M 1/3417* (2014.02); *A61M 1/36* (2013.01); *A61M 1/3626* (2013.01); *A61M 1/3638* (2014.02); *A61M 2205/3337* (2013.01); *A61M 2205/3344* (2013.01); *A61M 2205/3368* (2013.01)

(58) Field of Classification Search
CPC .... A61M 1/36; A61M 1/3424; A61M 1/3626; A61M 1/3638; A61M 2205/502; A61M 2205/3331; A61M 2205/3334; A61M 2205/3337; A61M 2205/3368; G06F 19/00; G16H 20/40; G16H 40/63; G16H 50/20; G16H 50/30
See application file for complete search history.

(56) References Cited

U.S. PATENT DOCUMENTS

| | | |
|---|---|---|
| 5,920,054 A | 7/1999 | Uber |
| 5,927,951 A | 7/1999 | Tamari |
| 6,044,691 A | 4/2000 | Kenley et al. |
| 6,374,084 B1 | 4/2002 | Fok |
| 6,497,680 B1 | 12/2002 | Holst |
| 6,868,720 B2 | 3/2005 | Lobdell |
| 7,147,616 B2 | 12/2006 | Pedrazzi et al. |
| 7,537,688 B2 | 5/2009 | Tarumi et al. |
| 7,618,531 B2 | 11/2009 | Sugioka et al. |
| 7,758,532 B2 | 7/2010 | Mori et al. |
| 7,959,593 B2 | 6/2011 | Ueda et al. |
| 8,011,905 B2 | 9/2011 | Artsyukhivich |
| 8,092,414 B2 | 1/2012 | Schnell et al. |
| 8,496,807 B2 | 7/2013 | Mori et al. |
| 8,960,010 B1 | 2/2015 | Crnkovich et al. |
| 9,192,708 B2 | 11/2015 | Iwahori et al. |
| 9,662,433 B2 | 5/2017 | Matsuo |
| 2003/0115965 A1 | 6/2003 | Mittelstein et al. |
| 2004/0129616 A1 | 7/2004 | Mori et al. |
| 2006/0043007 A1 | 3/2006 | Tarumi et al. |
| 2006/0074369 A1* | 4/2006 | Oishi ................ A61B 5/02152 604/4.01 |
| 2006/0079826 A1 | 4/2006 | Beden et al. |
| 2006/0226079 A1 | 10/2006 | Mori et al. |
| 2006/0289342 A1 | 12/2006 | Sugioka et al. |
| 2007/0108129 A1 | 5/2007 | Mori et al. |
| 2007/0118064 A1* | 5/2007 | Ueda ................... A61M 1/3644 422/44 |
| 2008/0103427 A1* | 5/2008 | Toyoda ............... A61M 1/3609 604/5.04 |
| 2009/0024070 A1 | 1/2009 | Gelfand et al. |
| 2009/0043240 A1 | 2/2009 | Robinson et al. |
| 2009/0312686 A1 | 12/2009 | Sakamoto et al. |
| 2010/0168640 A1 | 7/2010 | Kopperschmidt et al. |
| 2010/0234787 A1 | 9/2010 | Masaoka |
| 2010/0274172 A1 | 10/2010 | Guenther et al. |
| 2011/0089111 A1 | 4/2011 | Mori et al. |
| 2011/0139690 A1 | 6/2011 | Akita et al. |
| 2011/0213289 A1 | 9/2011 | Toyoda |
| 2012/0000547 A1 | 1/2012 | Gronau et al. |
| 2013/0035626 A1 | 2/2013 | Suzuki |
| 2013/0037480 A1* | 2/2013 | Wilt ..................... A61M 1/3413 210/321.69 |
| 2013/0150766 A1 | 6/2013 | Gambro |
| 2013/0150768 A1 | 6/2013 | Sakamoto et al. |
| 2013/0172803 A1 | 7/2013 | Gambro |
| 2013/0292313 A1 | 11/2013 | Fava et al. |
| 2014/0102983 A1 | 4/2014 | Meibaum et al. |
| 2014/0138301 A1 | 5/2014 | Iwahori et al. |
| 2014/0219829 A1 | 8/2014 | Matsuo et al. |
| 2015/0021244 A1 | 1/2015 | Furuhashi et al. |
| 2015/0150136 A1 | 6/2015 | Furuhashi et al. |
| 2015/0151036 A1* | 6/2015 | Furuhashi ............ A61M 1/3649 210/138 |
| 2015/0238675 A1 | 8/2015 | Carpani et al. |
| 2015/0238677 A1 | 8/2015 | Akita et al. |
| 2016/0250405 A1 | 9/2016 | Kogoshi et al. |
| 2017/0095602 A1 | 4/2017 | Ishizaki et al. |
| 2017/0173249 A1 | 6/2017 | Matshushita et al. |
| 2017/0312412 A1 | 11/2017 | Mochizuki et al. |
| 2018/0071449 A1 | 3/2018 | Hasegawa et al. |
| 2018/0080843 A1 | 3/2018 | Funamura et al. |
| 2018/0140766 A1 | 5/2018 | Mochizuki et al. |
| 2018/0228961 A1 | 8/2018 | Takeuchi et al. |
| 2018/0318490 A1 | 11/2018 | Naruse et al. |

FOREIGN PATENT DOCUMENTS

| | | |
|---|---|---|
| EP | 2361643 A1 | 8/2011 |
| EP | 2368583 A2 | 9/2011 |
| EP | 2535067 A1 | 12/2012 |
| EP | 2883558 A1 | 6/2015 |
| JP | S60-153138 U | 10/1985 |
| JP | S64-022357 U | 2/1989 |
| JP | H01-201263 A | 8/1989 |
| JP | H03-001290 | 1/1991 |
| JP | H03-073162 A | 3/1991 |
| JP | H06-047090 B2 | 2/1994 |
| JP | H08-510812 A | 11/1996 |
| JP | 2002-113096 A | 4/2002 |
| JP | 2003-093501 A | 4/2003 |
| JP | 2003-093503 A | 4/2003 |
| JP | 2003-519539 A | 6/2003 |
| JP | 2003-265601 A | 9/2003 |
| JP | 2003-290342 A | 10/2003 |
| JP | 2004-016619 A | 1/2004 |
| JP | 2004-049493 | 2/2004 |
| JP | 2004-049494 A | 2/2004 |
| JP | 2006-006836 | 6/2004 |
| JP | 2004-187990 A | 7/2004 |
| JP | 2004-313522 A | 11/2004 |
| JP | 2005-253555 A | 9/2005 |
| JP | 2006-280775 A | 10/2006 |
| JP | 2007-007435 A | 1/2007 |
| JP | 3128724 U | 1/2007 |
| JP | 2007-020962 A | 2/2007 |
| JP | 2007-135885 A | 6/2007 |
| JP | 2007-167108 A | 7/2007 |
| JP | 2007-236924 | 9/2007 |
| JP | 2007-268257 | 10/2007 |
| JP | 2007-282737 A | 11/2007 |
| JP | 2008-289635 A | 12/2008 |
| JP | 2009-112651 A | 5/2009 |
| JP | 2009-131412 A | 6/2009 |
| JP | 2009-525770 A | 7/2009 |
| JP | 2009-207706 A | 9/2009 |
| JP | 2010-273784 A | 12/2009 |
| JP | 2010-000161 A | 1/2010 |
| JP | 2010-029376 | 2/2010 |
| JP | 2010-136841 A | 6/2010 |
| JP | 2010-184029 A | 8/2010 |
| JP | 2010-188170 A | 9/2010 |
| JP | 2010-273693 A | 12/2010 |
| JP | 2011-030880 A | 2/2011 |
| JP | 2011-161060 A | 8/2011 |
| JP | 2012-034782 A | 2/2012 |
| JP | 2012-095842 A | 5/2012 |
| JP | 2012-095843 A | 5/2012 |
| JP | 2012-139405 A | 7/2012 |
| JP | 2012-192099 A | 10/2012 |
| JP | 2012-192100 A | 10/2012 |
| JP | 2012-192101 A | 10/2012 |
| JP | 2012-200340 A | 10/2012 |
| JP | 2013-027494 A | 2/2013 |
| JP | 2013-027495 A | 2/2013 |
| JP | 2013-056079 A | 3/2013 |
| JP | 2014-097197 A | 5/2014 |
| JP | 2014-184108 A | 10/2014 |
| JP | 5699008 B2 | 4/2015 |
| WO | 94/28309 A1 | 12/1994 |
| WO | 2001/051106 A1 | 7/2001 |
| WO | 2004/000391 A1 | 12/2003 |
| WO | 2005/118485 A1 | 12/2005 |
| WO | 2007/093064 A1 | 8/2007 |

(56) References Cited

FOREIGN PATENT DOCUMENTS

| WO | 2009/004777 A1 | 1/2009 |
| --- | --- | --- |
| WO | 2009/064741 A1 | 5/2009 |
| WO | 2009/074588 A1 | 6/2009 |
| WO | 2010/020390 A1 | 2/2010 |
| WO | 2011/099521 A1 | 8/2011 |
| WO | 2012/017959 A1 | 2/2012 |
| WO | 2013/031965 A1 | 3/2013 |
| WO | 2013/151114 A1 | 10/2013 |
| WO | 2014/024972 A1 | 2/2014 |
| WO | 2014/107656 A1 | 7/2014 |
| WO | 2015/068833 A1 | 5/2015 |

OTHER PUBLICATIONS

Chinese Office Action with Translation for Application No. 201780054724.6 dated Oct. 28, 2020.
International Search Report from the Japanese Patent Office for Application No. PCT/JP2017/002570 dated Feb. 28, 2017.
Co-pending U.S. Appl. No. 15/387,913 published as US2017/0095602A1 filed Dec. 22, 2016.
Co-pending U.S. Appl. No. 15/819,219 published as US2018/0071449A1 filed Nov. 21, 2017.
Co-pending U.S. Appl. No. 15/823,794 published as US2018/0080843A1 filed Nov. 28, 2017.
Co-pending U.S. Appl. No. 15/874,023 published as US2018/0140766A1 filed Jan. 18, 2018.
Co-pending U.S. Appl. No. 15/952,419 filed, published as US2018/0228961 filed Aug. 16, 2018.
Potentially Related Co-pending U.S. Appl. No. 16/037,170, published as US2018/0318490A1 filed Nov. 8, 2018.
(Online), 2015, (search date Dec. 6, 2017), internet: <URL: http://yanhd.net/cgi-bin/c-board/c-board.cgi?cmd=ntr;tree=16897;id=hd>, non-official translation (Regarding Retransfusion and Reinfusion from ECUM with Personal Dialysis Apparatus).
Extended European Search Report for corresponding European Application No. 17848907.6 dated Apr. 1, 2020.

* cited by examiner

[Fig. 1]
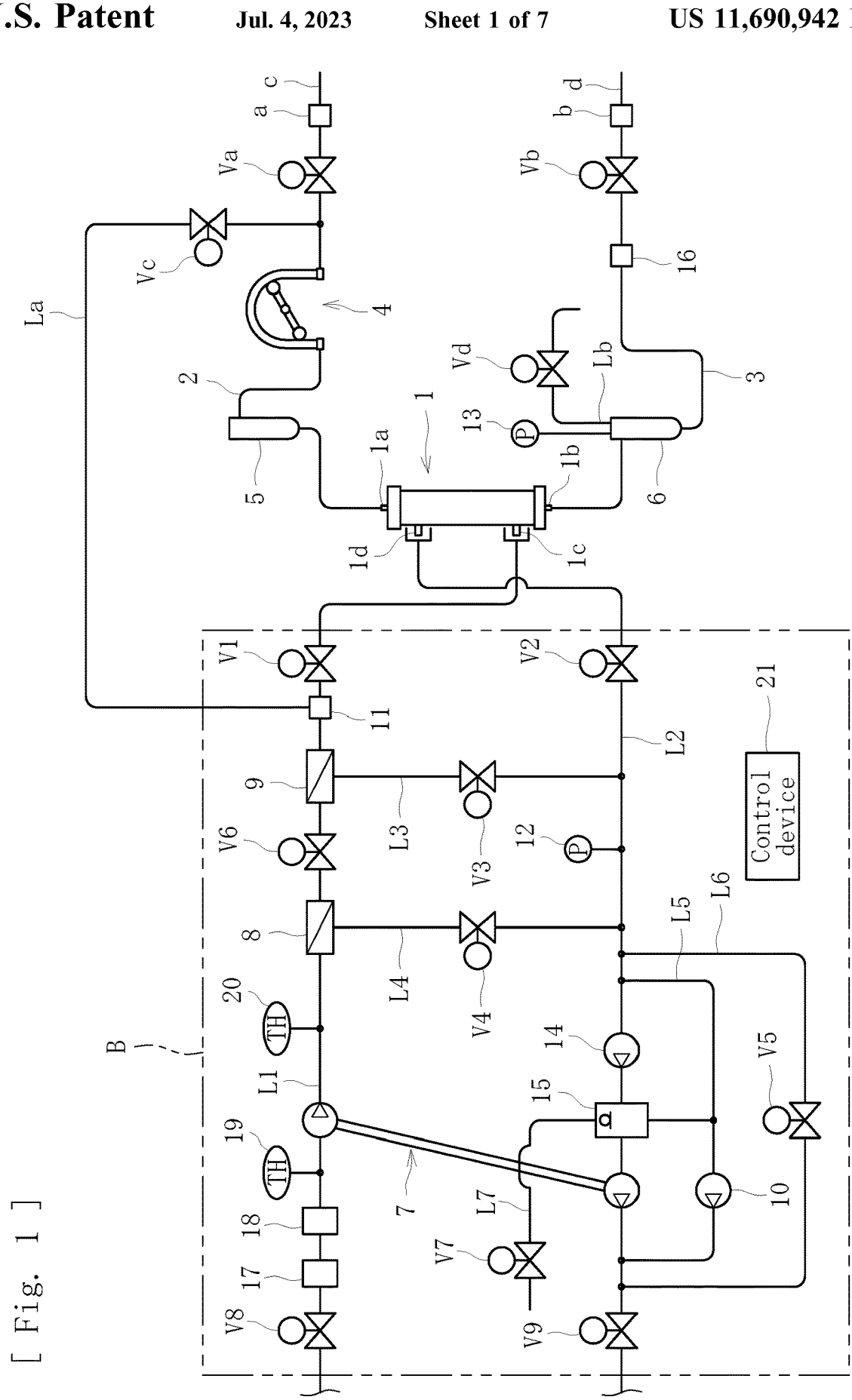

[Fig. 2]
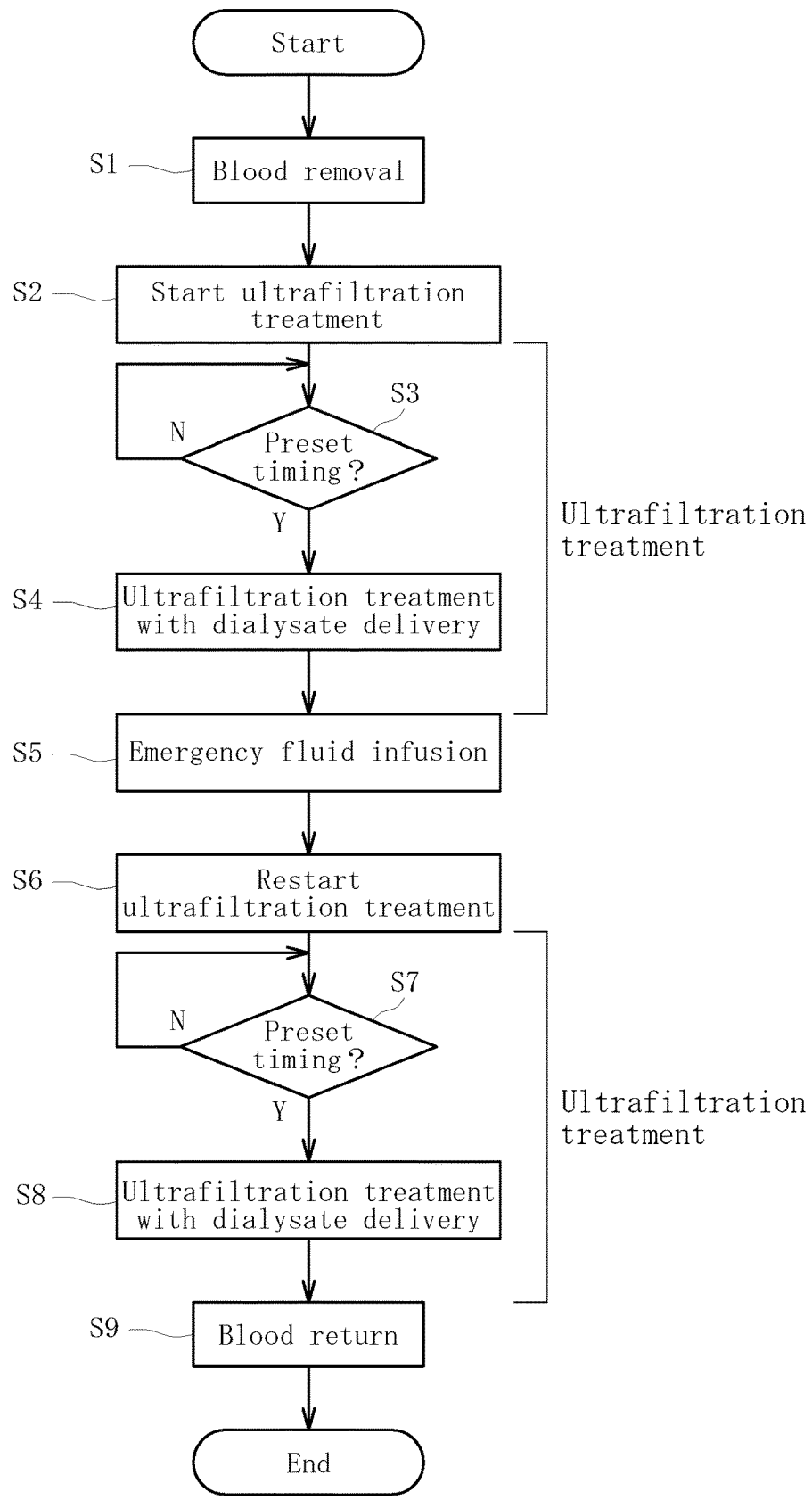

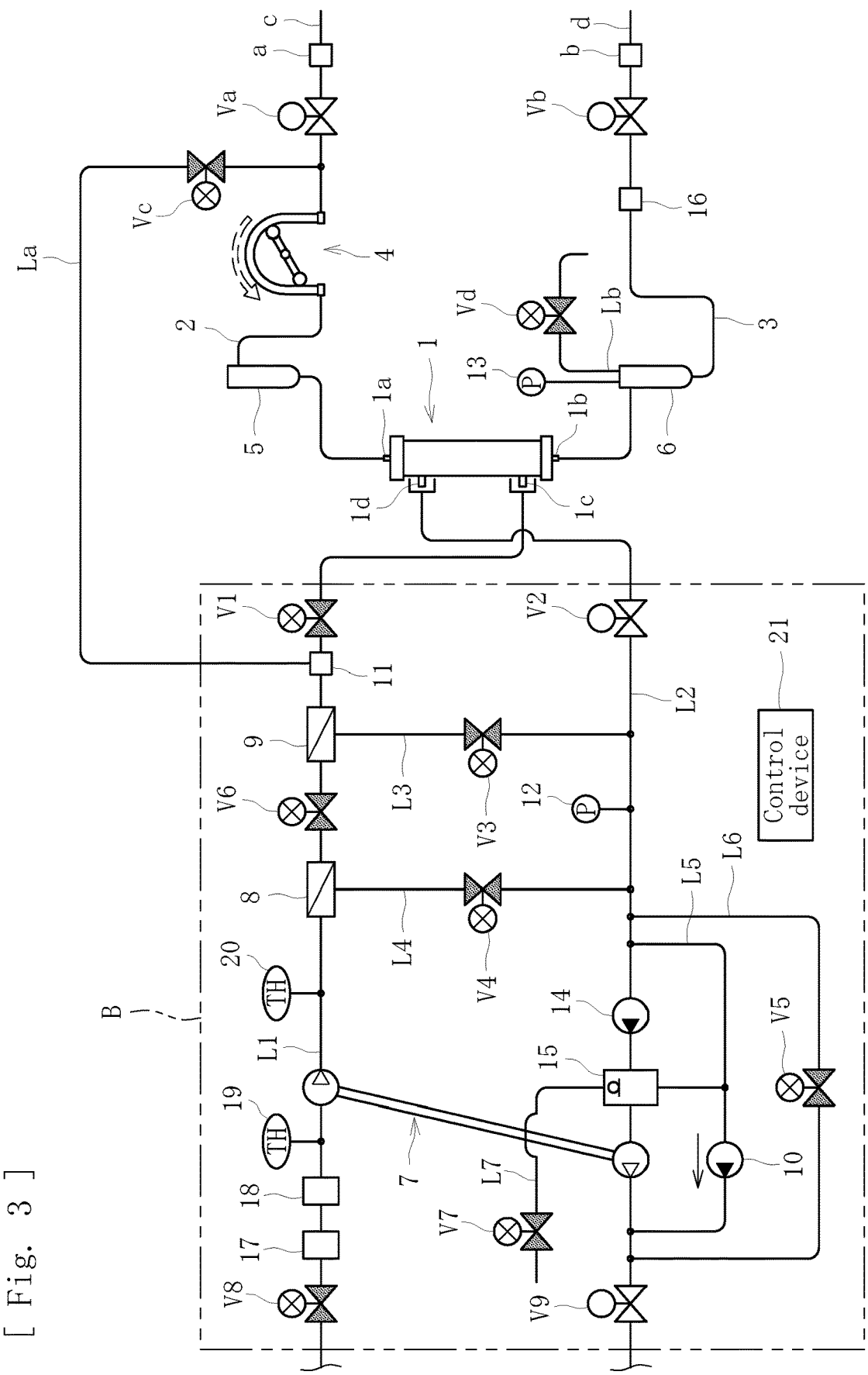
[Fig. 3]

[Fig. 4]
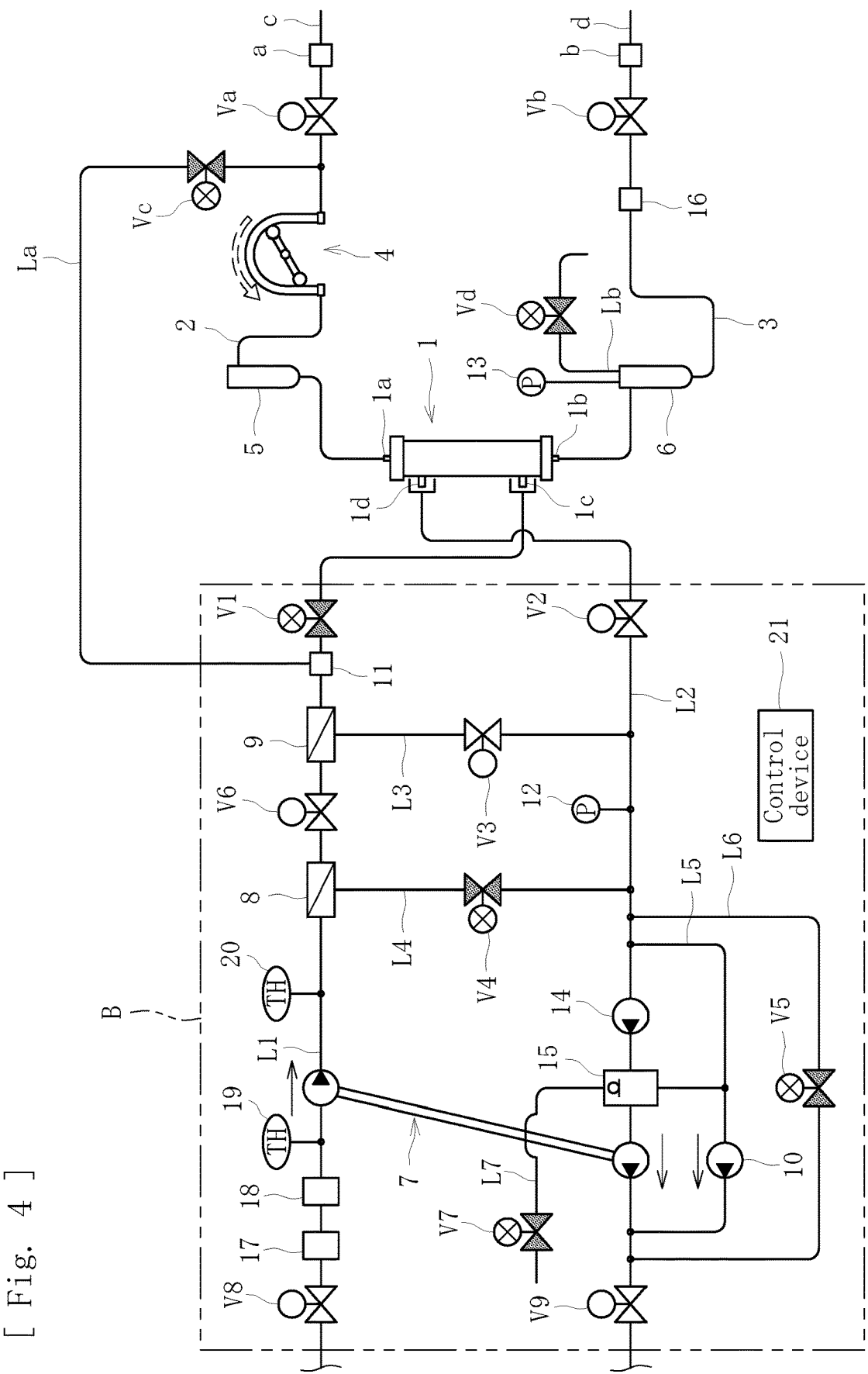

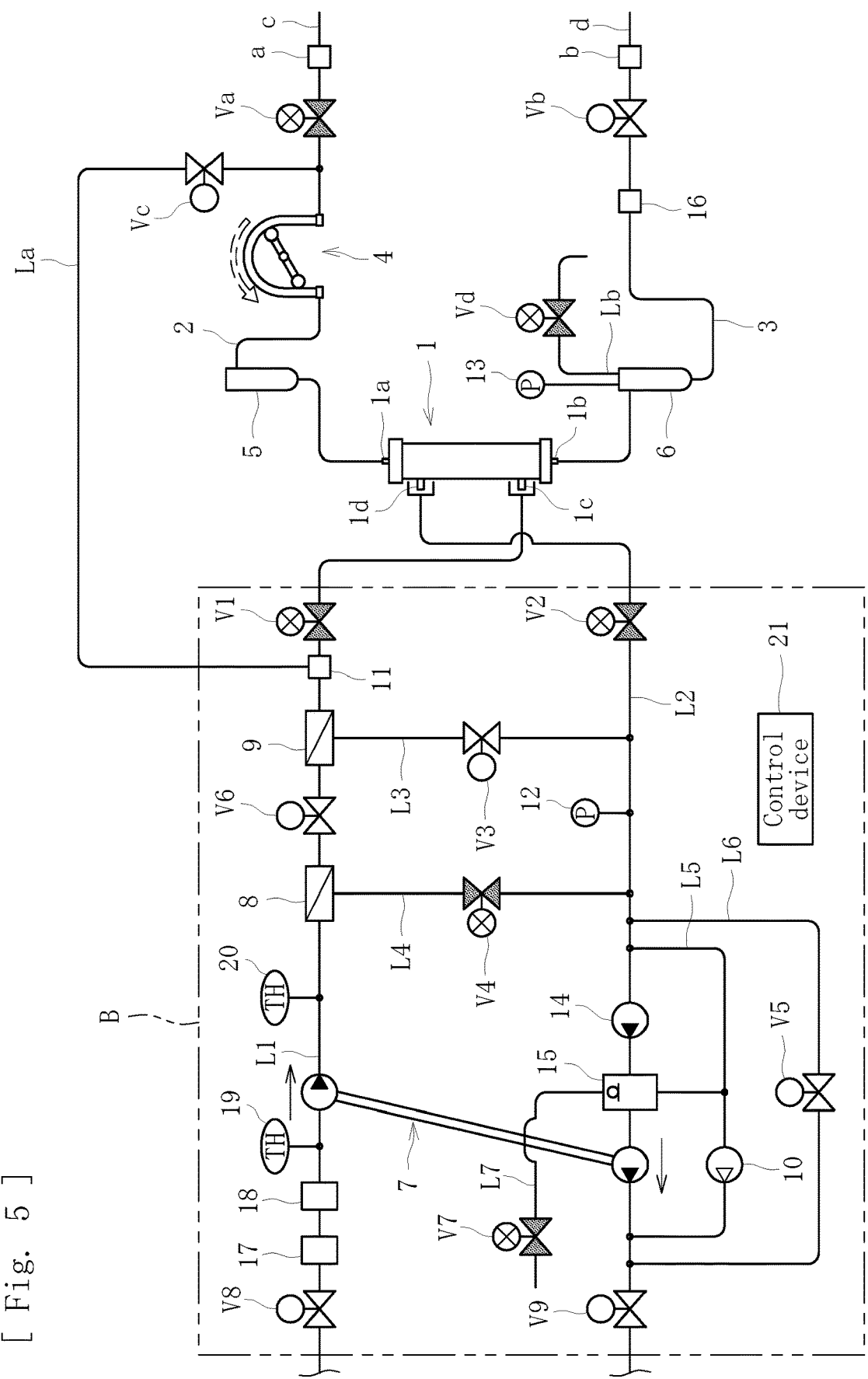
[Fig. 5]

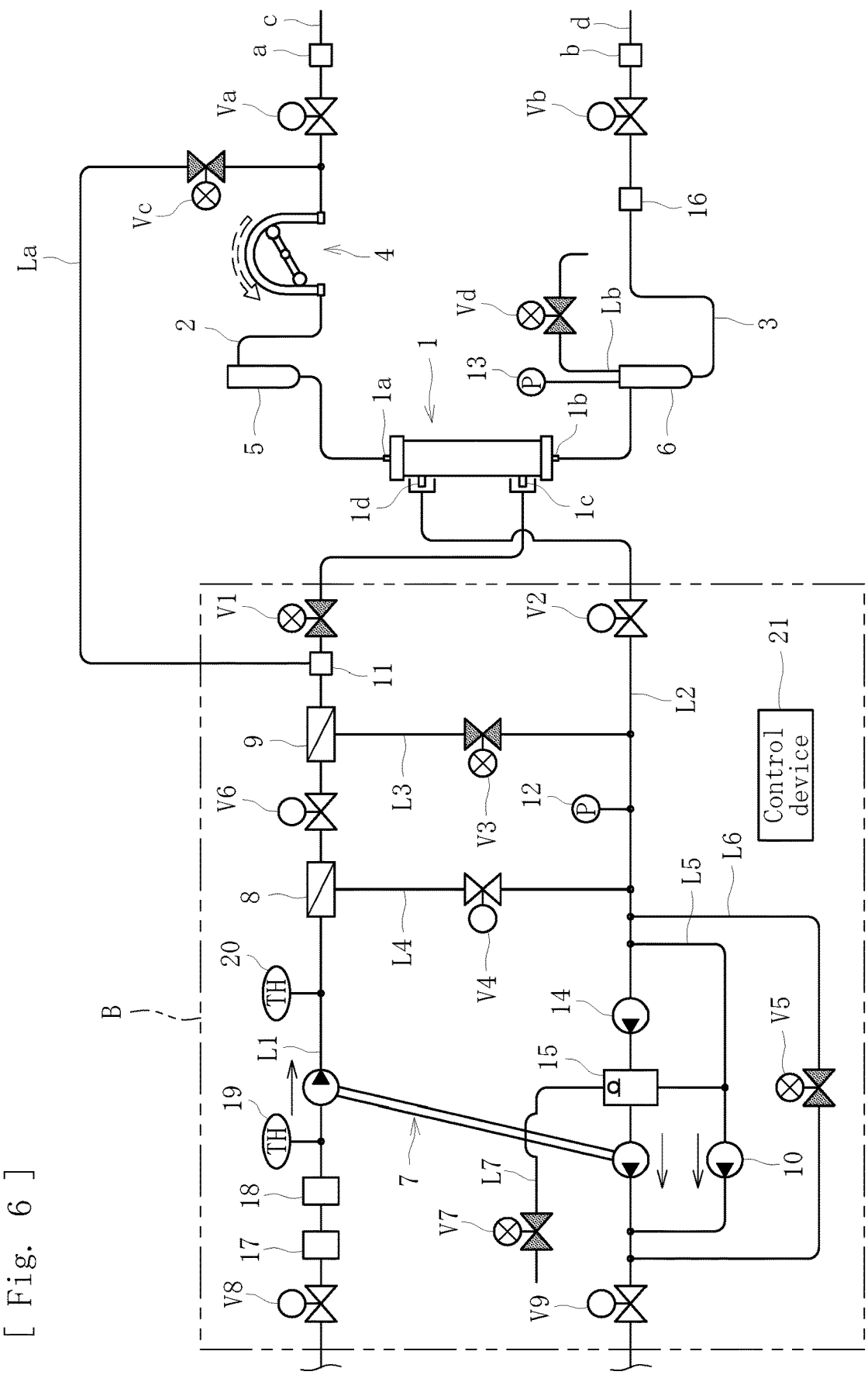
[Fig. 6]

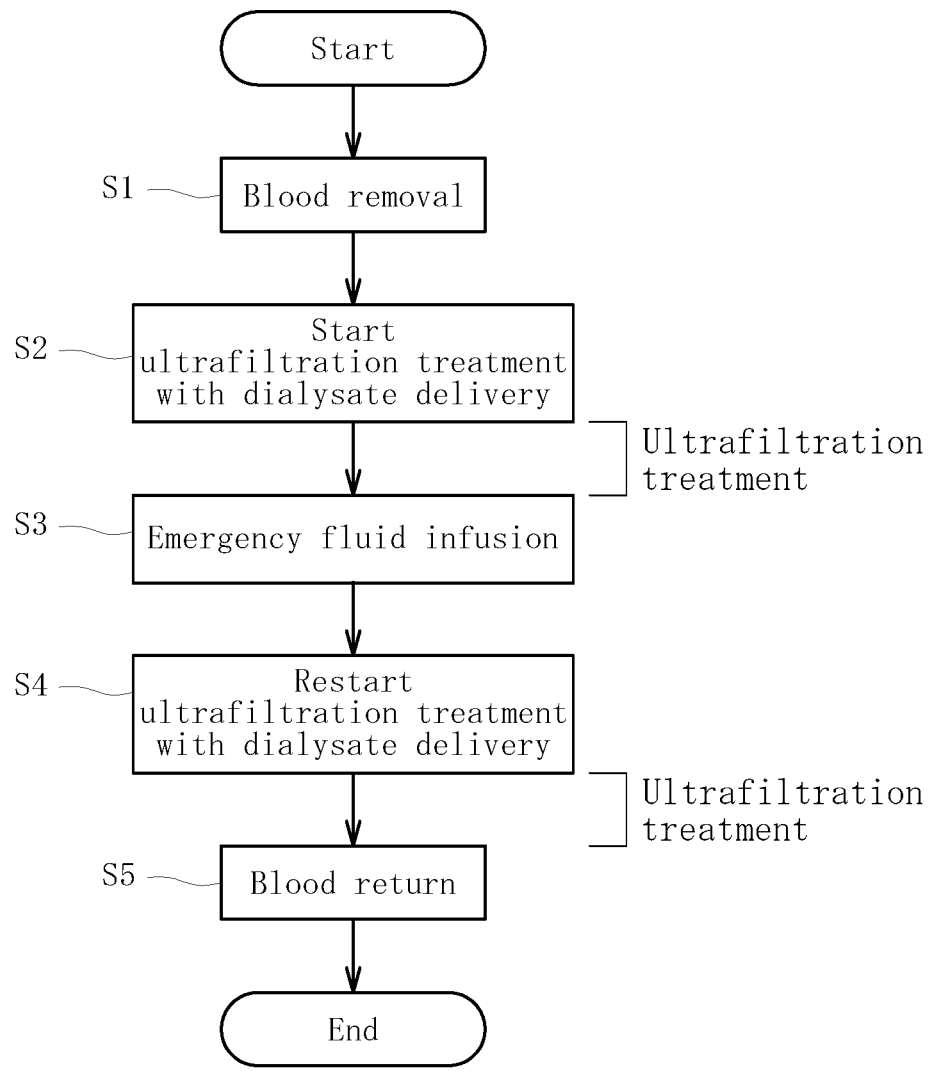

BLOOD PURIFICATION APPARATUS WITH A BYPASS LINE THAT BYPASSES AN ULTRAFILTRATION PUMP

FIELD

The present invention relates to a blood purification apparatus capable of performing substitution or blood return by supplying dialysate in a dialysate introduction line to a blood circuit.

BACKGROUND

Methods of blood purification treatment in which blood of a patient is purified through extracorporeal circulation of the blood include a treatment method called "ECUM" (extracorporeal ultrafiltration method) in which ultrafiltration alone is performed without supplying dialysate to a dialyzer, as disclosed by PTL 1, for example. In this "ECUM" (hereinafter referred to as "ultrafiltration treatment"), diffusion by the dialyzer is not performed. Therefore, the removal of solutes contained in the blood can be avoided. Hence, the reduction in blood pressure can be suppressed.

Typically, to perform such ultrafiltration treatment with a blood purification apparatus, an ultrafiltration pump is activated, with a dialysate introduction line for introducing dialysate into a dialyzer being closed by using an electromagnetic valve or the like so that the dialysate is not introduced into the dialyzer. With the effect of ultrafiltration by the dialyzer, ultrafiltration alone is performed on the blood that is extracorporeally circulating through a blood circuit.

PTL 1: Japanese Unexamined Patent Application Publication No. 2007-236924 the teachings of which are expressly incorporated by reference herein for all purposes.

SUMMARY OF INVENTION

However, if the above ultrafiltration treatment is performed with a blood purification apparatus that is capable of performing substitution (emergency fluid infusion) or blood return by supplying dialysate in a dialysate introduction line to a blood circuit, the following problem arises.

In the ultrafiltration treatment, a fluid delivering device (a duplex pump or the like) for delivering dialysate to the dialyzer is stopped. Therefore, the dialysate in the dialysate introduction line stagnates therein. Furthermore, a heating device, such as a heater, for heating the dialysate to be delivered to the dialyzer is also stopped.

Therefore, if the ultrafiltration treatment is continued for a long time, the composition or the concentration of the dialysate stagnated in the dialysate introduction line may change, or the temperature of the dialysate may drop to about room temperature. If the dialysate in such a state is supplied to the blood circuit, a problem may occur. Hence, to perform emergency fluid infusion during the ultrafiltration treatment or to perform blood return after the ultrafiltration treatment, some preparatory operations are necessary for causing the stagnated dialysate to flow by activating the fluid delivering device, and for heating the dialysate to be supplied to the blood circuit by activating the heating device. It is a problem that emergency fluid infusion or blood return cannot be performed during such preparatory operations.

The present invention has been conceived in view of the above circumstances and provides a blood purification apparatus that is capable of, with no preparatory operations, performing substitution by immediately supplying dialysate in a dialysate introduction line to a blood circuit during the ultrafiltration treatment, or performing blood return by immediately supplying the dialysate in the dialysate introduction line to the blood circuit after the ultrafiltration treatment.

DETAILED DESCRIPTION

According to the teachings herein, there is provided a blood purification apparatus comprising a blood circuit including an arterial blood circuit and a venous blood circuit through which blood of a patient extracorporeally circulates, a blood purification device provided between the arterial blood circuit and the venous blood circuit and that purifies the blood flowing in the blood circuit, a dialysate introduction line through which dialysate is introduced into the blood purification device, a dialysate drain line through which drain liquid from the blood purification device is drained, and an ultrafiltration pump removing water from the blood flowing in the blood circuit through the blood purification device. The blood purification apparatus performs substitution or blood return by supplying the dialysate in the dialysate introduction line to the blood circuit. In an ultrafiltration treatment in which the ultrafiltration pump is activated for ultrafiltration while the introduction of the dialysate into the blood purification device is stopped, dialysate delivery is performed while the introduction of the dialysate into the blood purification device is prevented.

According to the teachings herein, the blood purification apparatus taught herein further comprises a fluid delivering device delivering the dialysate in the dialysate introduction line to the blood purification device, a bypass line that bypasses the blood purification device and flows the dialysate in the dialysate introduction line into the dialysate drain line, and a closing device closing a flow route of the dialysate introduction line that extends between a connection to the bypass line and the blood purification device. During the ultrafiltration treatment, the flow route is closed by the closing device, and the dialysate that is delivered by the fluid delivering device flows into the bypass line.

According to the teachings herein, in the blood purification apparatus taught herein, the dialysate delivery during the ultrafiltration treatment is performed at a preset timing.

According to the teachings herein, in the blood purification apparatus taught herein, the preset timing is defined as a time based on a start time or an end time of the ultrafiltration treatment, or as a time when any condition for the treatment is changed.

According to the teachings herein, in the blood purification apparatus taught herein, the preset timing is defined in accordance with a parameter regarding a state of the patient or a state of the treatment that is detected during the ultrafiltration treatment.

According to the teachings herein, the blood purification apparatus taught herein further comprises a detection device detecting a temperature or a concentration of the dialysate in the dialysate introduction line. The preset timing is defined in accordance with the temperature or the concentration detected by the detection device during the ultrafiltration treatment.

According to the teachings herein, the blood purification apparatus taught herein further comprises a heating device heating the dialysate. During the ultrafiltration treatment, the dialysate is heated by the heating device while the dialysate delivery is performed.

According to the teachings herein, in the ultrafiltration treatment in which the ultrafiltration pump is activated for ultrafiltration while the introduction of the dialysate into the blood purification device is stopped, dialysate delivery is performed while the introduction of the dialysate into the blood purification device is prevented. Therefore, with no preparatory operations, substitution can be performed by immediately supplying the dialysate in the dialysate introduction line to the blood circuit during the ultrafiltration treatment, or blood return can be performed by immediately supplying the dialysate in the dialysate introduction line to the blood circuit after the ultrafiltration treatment.

According to the teachings herein, during the ultrafiltration treatment, the flow route is closed by the closing device, and the dialysate that is delivered by the fluid delivering device flows into the bypass line. Therefore, while the dialysate delivered by the fluid delivering device is caused to flow through the bypass line, the introduction of the dialysate into the blood purification device can be prevented.

According to the teachings herein, the dialysate delivery during the ultrafiltration treatment is performed at the preset timing. Therefore, the consumption of the dialysate can be made smaller and the cost can thus be reduced more than in a case where the dialysate continues to be delivered throughout the ultrafiltration treatment.

According to the teachings herein, the preset timing is defined as the time based on the start time or the end time of the ultrafiltration treatment or the time when any condition for the treatment is changed. Therefore, the dialysate can be delivered at an appropriate timing during the ultrafiltration treatment.

According to the teachings herein, the preset timing is defined in accordance with the parameter regarding the state of the patient or the state of the treatment that is detected during the ultrafiltration treatment. Therefore, the dialysate can be delivered at an appropriate timing corresponding to the state of the patient or the state of the treatment.

According to the teachings herein, the preset timing is defined in accordance with the temperature or the concentration that is detected by the detection device during the ultrafiltration treatment. Therefore, the dialysate can be delivered at an appropriate timing corresponding to the temperature or the concentration of the dialysate.

According to the teachings herein, during the ultrafiltration treatment, the dialysate is heated by the heating device while the dialysate delivery is performed. Therefore, the dialysate to be supplied to the blood circuit in the substitution performed during the ultrafiltration treatment or in the blood return performed after the ultrafiltration treatment can have an appropriate temperature.

BRIEF DESCRIPTION OF DRAWINGS

FIG. 1 is a schematic diagram of a blood purification apparatus according to a first embodiment of the present invention.

FIG. 2 is a flow chart of a control process for a treatment performed by the blood purification apparatus.

FIG. 3 is a schematic diagram of the blood purification apparatus in a state during an ultrafiltration treatment (without dialysate delivery).

FIG. 4 is a schematic diagram of the blood purification apparatus in a state during an ultrafiltration treatment (with dialysate delivery).

FIG. 5 is a schematic diagram of the blood purification apparatus in a state during emergency fluid infusion or blood return.

FIG. 6 is a schematic diagram of the blood purification apparatus in a state during another ultrafiltration treatment (with dialysate delivery).

FIG. 7 is a flow chart of a control process for a treatment performed by a blood purification apparatus according to a second embodiment of the present invention.

DESCRIPTION OF EMBODIMENTS

Embodiments of the present invention will now be described specifically with reference to the drawings.

A blood purification apparatus according to a first embodiment is applied to a hemodialysis apparatus and chiefly includes, as illustrated in FIG. 1, a blood circuit in which an arterial blood circuit 2 and a venous blood circuit 3 are connected to a dialyzer 1 serving as a blood purification device; a dialysis device B including a duplex pump 7, an ultrafiltration pump 10, a dialysate introduction line L1, and a dialysate drain line L2; a dialysate supply line La; and a control device 21.

The dialyzer 1 has non-illustrated blood purification membranes (hollow-fiber hemodialysis membranes or hemodiafiltration membranes in the first embodiment, or flat-film hemodialysis membranes or the like) therein and is provided with a blood introduction port 1a from which blood is introduced, a blood delivery port 1b from which the blood thus introduced is delivered, a dialysate introduction port 1c from which dialysate is introduced, and a dialysate drain port 1d from which the dialysate thus introduced is drained. The dialyzer 1 purifies the blood by bringing the dialysate into contact, through the hollow fiber membranes, with the blood introduced thereinto from the blood introduction port 1a.

The arterial blood circuit 2 is chiefly formed of a flexible tube, with one end thereof connected to the blood introduction port 1a of the dialyzer 1, thereby introducing blood collected from a blood vessel of a patient into the hollow fiber membranes provided in the dialyzer 1. The other end of the arterial blood circuit 2 is provided with a connector a to which an arterial puncture needle c is attachable. The arterial blood circuit 2 is also provided with an arterial air-trap chamber 5 for bubble removal and a blood pump 4 at respective halfway positions thereof. The blood pump 4 is a peristaltic pump (configured to squeeze the flexible tube when rotated in the normal direction, thereby causing the blood to flow from the side of the arterial puncture needle c toward the blood introduction port 1a of the dialyzer 1).

The venous blood circuit 3 is chiefly formed of a flexible tube, as with the arterial blood circuit 2, with one end thereof connected to the blood delivery port 1b of the dialyzer 1, thereby delivering the blood having flowed through the hollow fiber membranes out of the dialyzer 1. The other end of the venous blood circuit 3 is provided with a connector b to which a venous puncture needle d is attachable. The venous blood circuit 3 is also provided with a venous air-trap chamber 6 for bubble removal at a halfway position thereof. That is, the blood of the patient collected from the arterial puncture needle c flows through the arterial blood circuit 2, reaches the dialyzer 1, is purified therein, flows through the venous blood circuit 3, and returns into the body of the patient through the venous puncture needle d. Thus, the blood extracorporeally circulates. In this specification, the side of the puncture needle provided for blood removal (blood collection) is referred to as the "arterial" side, and the side of the puncture needle provided for returning the blood is referred to as the "venous" side. The "arterial" side and the "venous" side are not defined on the basis of which of the artery and the vein is to be the object of puncture.

The venous blood circuit 3 is provided with a bubble detection sensor 16 between a clamping device Vb and the venous air-trap chamber 6. The bubble detection sensor 16 is a sensor that is capable of detecting bubbles (air) in the liquid flowing in the blood circuit and includes, for example, a pair of ultrasonic transducers (an oscillator and a receiver) each being a piezoelectric device.

The arterial blood circuit 2 is provided with a clamping device Va on a distal side thereof (between the connector a and the blood pump 4 and near the connector a). The clamping device Va is capable of opening and closing a flow route. The venous blood circuit 3 is provided with the clamping device Vb on a distal side thereof (between the connector b and the venous air-trap chamber 6 and near the connector b). The clamping device Vb is capable of opening and closing a flow route. The venous air-trap chamber 6 provided at a halfway position of the venous blood circuit 3 is provided with an overflow line Lb extending from the top thereof. The overflow line Lb is provided with a clamping device Vd at a halfway position thereof. The clamping device Vd is capable of opening and closing a flow route.

Before performing dialysis treatment, the connector a and the connector b are connected to each other so that the distal end of the arterial blood circuit 2 and the distal end of the venous blood circuit 3 are joined to each other, whereby the arterial blood circuit 2 and the venous blood circuit 3 (including a blood flow route in the dialyzer 1 through which the blood flows) can form a closed circuit on the side of the blood circuit. If the dialysate as a priming solution is supplied to the closed circuit through the dialysate supply line La, the blood circuit (the arterial blood circuit 2 and the venous blood circuit 3) is filled with the dialysate, whereby a priming operation can be performed. In the priming operation, the dialysate is made to overflow through the overflow line Lb so that the inside of the closed circuit on the side of the blood circuit can be flushed with the dialysate.

The venous air-trap chamber 6 is provided with a venous-pressure sensor 13 that is capable of detecting the hydraulic pressure (venous pressure) in the venous blood circuit 3 by detecting the pressure of an air layer, which is produced on the upper side of the venous air-trap chamber 6, while the blood is extracorporeally circulating through the blood circuit. When blood purification treatment is started and the blood of the patient is caused to extracorporeally circulate through the blood circuit, the venous pressure detected by the venous-pressure sensor 13 can be monitored.

An end of the dialysate introduction line L1 and an end of the dialysate drain line L2 are connected to the dialysate introduction port 1*c* and the dialysate drain port 1*d*, respectively, of the dialyzer 1. The dialysate introduced into the dialyzer 1 through the dialysate introduction line L1 flows outside the hollow fiber membranes and is allowed to be drained through the dialysate drain line L2. Thus, the inside of each of the hollow fiber membranes (purification membranes) provided in the dialyzer 1 forms a blood flow route in which blood is allowed to flow, whereas the outside of each of the hollow fiber membranes forms a dialysate flow route in which dialysate is allowed to flow.

The dialysis device B including the dialysate introduction line L1 and the dialysate drain line L2 further includes the duplex pump 7, bypass lines L3 to L6, and electromagnetic valves V1 to V9. The duplex pump 7 is provided over the dialysate introduction line L1 and the dialysate drain line L2. The duplex pump 7 causes a dialysate prepared to have a predetermined concentration to be introduced into the dialyzer 1 and also causes the dialysate used for dialysis to be drained from the dialyzer 1. That is, the duplex pump 7 according to the first embodiment forms a "fluid delivering device" that is capable of delivering the dialysate in the dialysate introduction line L1 to the dialyzer 1 when activated. The duplex pump 7 may be replaced with a fluid delivering device of another type (not limited to a pump and may be a balance chamber or the like) that is capable of delivering the dialysate in the dialysate introduction line L1 to the dialyzer 1.

The dialysate introduction line L1 is provided with the electromagnetic valve V1 at a halfway position thereof (on the downstream side (nearer to the dialyzer 1) with respect to a joint of the dialysate introduction line L1 to the dialysate supply line La). The dialysate drain line L2 is provided with the electromagnetic valve V2 at a halfway position thereof (on the upstream side (nearer to the dialyzer 1) with respect to a joint of the dialysate drain line L2 to the bypass line L3). The electromagnetic valve V1 forms a "closing device" that is capable of closing a flow route extending between a connection of the dialysate introduction line L1 to the below-described bypass line (the bypass line L3 or L4) and the dialyzer 1.

The dialysate introduction line L1 is also provided with a heater 17 (a heating device) capable of heating the dialysate delivered by the duplex pump 7 (the fluid delivering device), a concentration sensor 18 (a detection device) capable of detecting the concentration of the dialysate in the dialysate introduction line L1, and temperature sensors 19 and 20 (detection devices) each capable of detecting the temperature of the dialysate in the dialysate introduction line L1. The heater 17, the concentration sensor 18, and the temperature sensor 19 are provided on the upstream side with respect to the position of the duplex pump 7. The temperature sensor 20 is provided on the downstream side with respect to the position of the duplex pump 7. The dialysate introduction line L1 is provided with the electromagnetic valve V8 on the upstream side with respect to the heater 17. The dialysate drain line L2 is provided with the electromagnetic valve V9 (on the downstream side with respect to a connection thereof to the bypass line L6).

The dialysate introduction line L1 is also provided with filters 8 and 9 between the duplex pump 7 and the electromagnetic valve V1. The filters 8 and 9 filter and thus purify the dialysate flowing in the dialysate introduction line L1. The bypass lines L3 and L4 are connected to the filters 8 and 9, respectively, thereby providing bypasses for the dialysate to be introduced into the dialysate drain line L2.

The bypass lines L3 and L4 are provided with the electromagnetic valves V3 and V4, respectively. When the electromagnetic valve V3 or V4 is opened so that the flow route is opened, the dialysate in the dialysate introduction line L1 is allowed to bypass the dialyzer 1 and to flow into the dialysate drain line L2. The dialysate introduction line L1 is provided with the electromagnetic valve V6 between the filter 8 and the filter 9.

The dialysate drain line L2 is provided with a hydraulic-pressure-measuring sensor 12 between the joint to the bypass line L3 and a joint to the bypass line L4. The hydraulic-pressure-measuring sensor 12 is capable of measuring the hydraulic pressure of the dialysate. The dialysate drain line L2 is also provided with the bypass lines L5 and L6 each connected thereto and bypassing the drain side of the duplex pump 7. The bypass line L5 is provided with the ultrafiltration pump 10 for removing water from the blood of the patient flowing in the dialyzer 1. The bypass line L6 is provided with the electromagnetic valve V5 capable of opening and closing a flow route.

The dialysate drain line L2 is provided with a pressurizing pump 14 on the upstream side with respect to the duplex pump 7 (between a joint to the bypass line L5 and the duplex pump 7). The pressurizing pump 14 adjusts the hydraulic pressure on the drain side of the duplex pump 7. Furthermore, the dialysate drain line L2 is provided with a degassing chamber 15 on the upstream side with respect to the duplex pump 7 (between the pressurizing pump 14 and the duplex pump 7). The degassing chamber 15 is provided with an atmosphere release line L7 connected thereto with a check valve or the like interposed therebetween. The atmosphere release line L7 is provided with the electromagnetic valve V7.

The dialysate supply line La is connected at one end thereof to a collection port 11 (a so-called sampling port) provided on the dialysate introduction line L1, and at the other end thereof to the arterial blood circuit 2 (or the venous blood circuit 3). The dialysate supply line La forms a flow route that allows the dialysate in the dialysate introduction line L1 to be supplied to the arterial blood circuit 2 (or the venous blood circuit 3). The dialysate supply line La is provided with a clamping device Vc capable of opening and closing a flow route. When the clamping device Vc is opened, the dialysate is allowed to be supplied to the blood circuit through the dialysate supply line La, so that priming before the treatment, substitution (emergency fluid infusion) during the treatment, or blood return after the treatment can be performed.

The control device 21 is a microcomputer or the like provided in, for example, the dialysis device B and is capable of controlling operations such as the opening and closing of any of the electromagnetic valves V1 to V9, the opening and closing of any of the clamps (Va to Vd), the activation and stopping of any of the actuators including the duplex pump 7 and the blood pump 4, and the activation of the heater 17 (the heating device). The control device 21 is electrically connected to the sensors including the hydraulic-pressure-measuring sensor 12, the venous-pressure sensor 13, the bubble detection sensor 16, the concentration sensor 18 (the detection device), and the temperature sensors 19 and 20 (the detection devices). The dialysate drain line L2 may also be provided with a drain-liquid-concentration sensor capable of detecting the concentration of drain liquid, a blood-pressure sensor capable of detecting the blood pressure of the patient during the treatment, and the like, so that the detected values of such sensors can be monitored.

In the first embodiment, substitution (emergency fluid infusion) during the treatment or blood return after the treatment can be performed by supplying the dialysate in the dialysate introduction line L1 to the blood circuit. Emergency fluid infusion is an operation of supplying the dialysate as a substitution fluid to the blood circuit in a situation where the blood pressure of the patient has dropped excessively during the treatment, or any other like situation. Blood return is an operation of returning the blood remaining in the blood circuit to the patient by supplying the dialysate as a substitution fluid to the blood circuit after the treatment.

The control device 21 is capable of initiating the ultrafiltration treatment (an "ECUM" operation) in which ultrafiltration is performed by activating the ultrafiltration pump 10 while stopping the introduction of the dialysate into the dialyzer 1. Specifically, as illustrated in FIGS. 3 and 4, the blood is caused to extracorporeally circulate through the blood circuit by activating the blood pump 4. In this state, the ultrafiltration pump 10 is activated. Then, with the effect of ultrafiltration, water is removed from the blood flowing in the hollow fiber membranes of the dialyzer 1, and the water is drained through the dialysate drain line L2. Thus, the ultrafiltration treatment is performed. In such a method, diffusion by the dialyzer 1 is not performed, and ultrafiltration alone can be performed. Therefore, the reduction in plasma osmolality caused by the removal of substances (urea and creatinine) from the blood by diffusion can be suppressed.

As illustrated in FIG. 4, the control device 21 according to the first embodiment is capable of controlling the duplex pump 7 (the fluid delivering device) to deliver the dialysate while preventing the introduction of the dialysate into the dialyzer 1 during the ultrafiltration treatment. Specifically, as described above, ultrafiltration alone is performed with no diffusion by the dialyzer 1. Furthermore, as illustrated in FIG. 4, the electromagnetic valve V1 (the closing device) is closed but the electromagnetic valve V3 is opened, whereby the flow route to the dialyzer 1 is closed, and the dialysate delivered by the duplex pump 7 (the fluid delivering device) is made to flow into the bypass line L3.

Thus, even during the ultrafiltration treatment, the dialysate in the dialysate introduction line L1 can be caused to flow into the dialysate drain line L2 through the bypass line L3 and further be discharged to the outside. Therefore, the stagnation of the dialysate in the dialysate introduction line L1 can be prevented. Furthermore, the reduction in the temperature of the dialysate can be prevented by the heating with the heater 17. Hence, it is possible to perform substitution by immediately supplying the dialysate in the dialysate introduction line L1 to the blood circuit during the ultrafiltration treatment, or to perform blood return by immediately supplying the dialysate in the dialysate introduction line L1 to the blood circuit after the ultrafiltration treatment.

In particular, in the first embodiment, the delivery of the dialysate by the duplex pump 7 (the fluid delivering device) during the ultrafiltration treatment is controlled to be performed at a preset timing. That is, when the ultrafiltration treatment is started, as illustrated in FIG. 3, the duplex pump 7 is stopped so that the flow of the dialysate in the dialysate introduction line L1 is stopped. Meanwhile, the blood pump 4 is activated so that the blood extracorporeally circulates through the blood circuit. In this state, the ultrafiltration pump 10 is activated. Hence, ultrafiltration alone is performed with no diffusion by the dialyzer 1. As illustrated in FIG. 4, the duplex pump 7 is activated at a preset timing while the blood pump 4 and the ultrafiltration pump 10 are kept active. Thus, the dialysate in the dialysate introduction line L1 is caused to flow into the dialysate drain line L2 through the bypass line L3.

The preset timing (the timing of activating the duplex pump 7 during the ultrafiltration treatment) can be defined as the time based on the start time or the end time of the ultrafiltration treatment, or as the time when any condition for the treatment is changed. For example, the preset timing may be every period of time between the start and the end of the treatment, the time after a predetermined period from the start of the treatment, the time before the end of the treatment by a predetermined period, the time when the blood pressure of the patient is estimated to drop on the basis of the treatment history of that patient, or the like. Alternatively, dialysate delivery by the duplex pump 7 (the fluid delivering device) may be performed if any change (any change in conditions for the treatment) as a trigger, such as lowering of a set value of the ultrafiltration rate or the blood flow rate on the basis of a determination made by a medical staff or the like, is detected during the ultrafiltration treatment.

The preset timing may also be defined in accordance with a parameter regarding the state of the patient or the state of the treatment that is detected during the ultrafiltration treatment. For example, the parameter may be the blood pressure value, the hematocrit value, ΔBV (circulating blood volume rate of change), or PRR (plasma refilling rate) of the patient that is detected or calculated during the treatment, or any other parameter detected by a DDM (dialysis dose monitor). The blood pressure value is preferably detected by using a sphygmomanometer included in the blood purification apparatus. The sphygmomanometer is preferably of a type in which the blood pressure of the patient is detected regularly at predetermined intervals with a cuff attached to the patient. The hematocrit value is preferably detected by using a hematocrit sensor provided to the blood circuit.

The parameter ΔBV (circulating blood volume rate of change) is calculated from the hematocrit value (or the hemoglobin concentration, the total protein concentration of the serum, or the like) detected during the treatment, and is an index representing the rate of change in the volume of blood in the blood vessel of the patient. The parameter PRR (plasma refilling rate) is an index representing the allowance for the refilling of blood with interstitial fluid outside the blood vessel (plasma refilling) that is caused by ultrafiltration. A decrease in ΔBV or PRR indicates a reduction in blood pressure. Hence, if ΔBV or PRR decreases to a predetermined value or lower, it can be assumed that substitution is to be performed. Note that the rate of decrease in ΔBV or PRR varies with individuals. Hence, it is preferable to set these parameters individually for each patient.

A DDM (dialysis dose monitor) is provided to, for example, the dialysate drain line L2. The DDM is a monitor that measures the change in ultraviolet absorbance of the drained dialysate, thereby being capable of calculating the change in blood urea nitrogen that correlates with the change in absorbance, and calculating parameters such as Kt/V (standardized dialysis dose) and URR (urea reduction ratio). The increase in Kt/V (standardized dialysis dose) or URR (urea reduction ratio) indicates the progress of the treatment (the state of the treatment). Therefore, the timing of activation of the duplex pump 7 during the ultrafiltration treatment can be defined as the time when such a parameter has exceeded a predetermined threshold.

The preset timing may also be defined in accordance with the temperature or the concentration detected by the concentration sensor 18 or the temperature sensor (19 or 20) (the detection device) during the ultrafiltration treatment. For example, during the ultrafiltration treatment, if the concentration or the temperature of the dialysate detected by the concentration sensor 18 or the temperature sensor (19 or 20) is lower than or equal to a predetermined value, the heater 17 is activated and the duplex pump 7 is activated, whereby the dialysate in the dialysate introduction line L1 is caused to flow into the dialysate drain line L2 through the bypass line L3. Thus, the dialysate can be supplied immediately to the blood circuit at the time of substitution or blood return.

The preset timing may also be defined as the time when the dialyzer differential pressure (the differential pressure between the hydraulic pressure of the arterial blood circuit 2 near the inlet of the dialyzer 1 and the hydraulic pressure of the venous blood circuit 3 near the outlet of the dialyzer 1) or TMP (the differential pressure between the hydraulic pressure of the blood flow route in which the blood flows and the hydraulic pressure of the dialysate flow route in which the dialysate flows) has reached a predetermined value. The dialyzer differential pressure or TMP exceeding a threshold is regarded as indicating the occurrence of clogging in the hollow fiber membranes of the dialyzer 1. Therefore, the treatment is assumed to be suspended for blood return.

Now, a control process performed by the control device 21 according to the first embodiment will be described with reference to the flow chart illustrated in FIG. 2 and to FIGS. 3 to 5.

First, the blood pump 4 is activated with the arterial puncture needle c and the venous puncture needle d being stuck in the patient, whereby the blood of the patient is removed and is taken into the blood circuit (S1). Subsequently, as illustrated in FIG. 3, the clamping devices (Vc and Vd) are closed while the clamping devices (Va and Vb) are opened on the side of the blood circuit. Furthermore, the electromagnetic valves (V1 and V3 to V8) are closed while the electromagnetic valves (V2 and V9) are opened on the side of the dialysis device B. Furthermore, with the duplex pump 7 being stopped, the ultrafiltration pump 10 is activated while the blood pump 4 is kept active, whereby an ultrafiltration treatment is started (S2).

In the ultrafiltration treatment started in step S2, since the blood pump 4 is active, the blood extracorporeally circulates through the blood circuit. Furthermore, since the ultrafiltration pump 10 is activated, water is removed, by the effect of ultrafiltration, from the blood flowing in the hollow fiber membranes of the dialyzer 1 and is drained through the dialysate drain line L2. During the ultrafiltration treatment, the dialysate in the dialysate introduction line L1 stagnates therein. Therefore, the heater 17 is stopped.

Subsequently, while the ultrafiltration treatment is in progress, whether or not the preset timing has reached is checked (S3). As described above, the preset timing is defined as the timing at which substitution, if performed, is acceptable immediately. Preferably, for example, the preset timing is defined as the time based on the start time or the end time of the ultrafiltration treatment, or as the time when any condition for the treatment is changed; or is defined in accordance with a parameter regarding the state of the patient or the state of the treatment that is detected during the ultrafiltration treatment, or in accordance with the temperature or the concentration detected by the detection device such as the concentration sensor 18 or the temperature sensor (19 or 20) during the ultrafiltration treatment.

In step S3, if it is determined that the preset timing has reached, the process proceeds to step S4, where the duplex pump 7 is activated to deliver the dialysate while the introduction of the dialysate into the dialyzer 1 is prevented. In such an ultrafiltration treatment in which dialysate delivery is performed, as illustrated in FIG. 4, the clamping devices (Vc and Vd) are closed while the clamping devices (Va and Vb) are opened on the side of the blood circuit. Furthermore, the electromagnetic valves (V1, V4, V5, and V7) are closed while the electromagnetic valves (V2, V3, V6, V8, and V9) are opened on the side of the dialysis device B. Then, with the duplex pump 7 being active, the ultrafiltration pump 10 is activated while the blood pump 4 is kept active, whereby the ultrafiltration treatment with dialysate delivery is performed.

In the ultrafiltration treatment performed in step S4, since the blood pump 4 is active, the blood extracorporeally circulates through the blood circuit. Furthermore, since the ultrafiltration pump 10 is activated, water is removed, by the effect of ultrafiltration, from the blood flowing in the hollow fiber membranes of the dialyzer 1 and is drained through the dialysate drain line L2. Meanwhile, since the duplex pump 7 is active, the dialysate is caused to flow through the dialysate introduction line L1, the bypass line L3, and the dialysate drain line L2. During this ultrafiltration treatment, the dialysate in the dialysate introduction line L1 stops stagnating, and the heater 17 is activated to heat the dialysate.

Subsequently, if emergency fluid infusion is necessary, emergency fluid infusion is performed in step S5. In this emergency fluid infusion, as illustrated in FIG. 5, the clamping devices (Va and Vd) are closed while the clamping devices (Vb and Vc) are opened on the side of the blood circuit. Furthermore, the electromagnetic valves (V1, V2, V4, and V7) are closed while the electromagnetic valves (V3, V5, V6, V8, and V9) are opened on the side of the dialysis device B. Then, with the duplex pump 7 being active, the ultrafiltration pump 10 is stopped while the blood pump 4 is kept active, whereby the dialysate in the dialysate introduction line L1 is supplied to the blood circuit through the dialysate supply line La and is introduced as a substitution fluid into the body of the patient so as to counteract the reduction in blood pressure.

The above emergency fluid infusion in step S5 is performed after the ultrafiltration treatment with dialysate delivery performed in step S4. Therefore, the dialysate heated to a preset temperature by the heater 17 or having a preset concentration (composition) can be supplied to the blood circuit. Hence, no preparatory operations are necessary, and substitution can be performed by immediately supplying the dialysate in the dialysate introduction line L1 to the blood circuit during the ultrafiltration treatment. After substitution is performed as above, the ultrafiltration treatment without dialysate delivery illustrated in FIG. 3 (details have been described above) is restarted (S6). In this process, it is checked whether or not the preset timing has reached (S7).

As described above, the preset timing is defined as the timing at which blood return, if performed, is acceptable immediately. Preferably, for example, the preset timing is defined as the time based on the start time or the end time of the ultrafiltration treatment, or as the time when any condition for the treatment is changed; or is defined in accordance with a parameter regarding the state of the patient or the state of the treatment that is detected during the ultrafiltration treatment, or in accordance with the temperature or the concentration detected by the detection device such as the concentration sensor 18 or the temperature sensor (19 or 20) during the ultrafiltration treatment. In step S7, if it is determined that the preset timing has reached, the process proceeds to step S8, where, as illustrated in FIG. 4, the ultrafiltration treatment with dialysate delivery is performed by activating the duplex pump 7 while preventing the introduction of the dialysate into the dialyzer 1 (details have been described above).

Subsequently, if blood return after the treatment is to be performed, blood return is performed in step S9. In this blood return, as illustrated in FIG. 5, the clamping devices (Va and Vd) are closed while the clamping devices (Vb and Vc) are opened on the side of the blood circuit. Furthermore, the electromagnetic valves (V1, V2, V4, and V7) are closed while the electromagnetic valves (V3, V5, V6, V8, and V9) are opened on the side of the dialysis device B. Then, with the duplex pump 7 being active, the ultrafiltration pump 10 is stopped while the blood pump 4 is kept active, whereby the dialysate in the dialysate introduction line L1 is supplied to the blood circuit through the dialysate supply line La and is substituted for the blood in the blood circuit. Thus, the blood in the blood circuit can be returned to the patient.

The blood return in step S9 is performed after the ultrafiltration treatment with dialysate delivery performed in step S8. Therefore, the dialysate heated to a preset temperature by the heater 17 or having a preset concentration (composition) can be supplied to the blood circuit. Hence, no preparatory operations are necessary, and blood return can be performed by immediately supplying the dialysate in the dialysate introduction line L1 to the blood circuit after the ultrafiltration treatment. This is the end of the blood purification treatment.

According to the first embodiment, in the ultrafiltration treatment in which the ultrafiltration pump 10 is activated for ultrafiltration while the introduction of the dialysate into the dialyzer 1 is stopped, dialysate delivery is performed while the introduction of the dialysate into the dialyzer 1 is prevented. Therefore, with no preparatory operations, substitution can be performed by immediately supplying the dialysate in the dialysate introduction line L1 to the blood circuit during the ultrafiltration treatment, or blood return can be performed by immediately supplying the dialysate in the dialysate introduction line L1 to the blood circuit after the ultrafiltration treatment. In the first embodiment, the ultrafiltration treatment with dialysate delivery is performed with the activation of the duplex pump 7. Alternatively, dialysate delivery may be performed by another fluid delivering device.

Furthermore, during the ultrafiltration treatment, the flow route is closed by the electromagnetic valve V1 (the closing device), and the dialysate that is delivered by the duplex pump 7 (the fluid delivering device) is caused to flow into the bypass line L3. Therefore, while the dialysate delivered by the duplex pump 7 is caused to flow through the bypass line L3, the introduction of the dialysate into the dialyzer 1 can be prevented. According to the first embodiment, in the ultrafiltration treatment with dialysate delivery, the electromagnetic valve V3 is opened so as to cause the dialysate to flow through the bypass line L3. Alternatively, as illustrated in FIG. 6, the electromagnetic valve V4 may be opened so as to cause the dialysate to flow through the bypass line L4.

Furthermore, the dialysate delivery during the ultrafiltration treatment is performed at a preset timing. Therefore, the consumption of the dialysate can be made smaller and the cost can thus be reduced more than in a case where the dialysate continues to be delivered throughout the ultrafiltration treatment. If the preset timing is defined as the time based on the start time or the end time of the ultrafiltration treatment or the time when any condition for the treatment is changed, the dialysate can be delivered at an appropriate timing during the ultrafiltration treatment.

Furthermore, the preset timing is defined in accordance with a parameter regarding the state of the patient or the state of the treatment that is detected during the ultrafiltration treatment. Therefore, the dialysate can be delivered at an appropriate timing corresponding to the state of the patient or the state of the treatment. Furthermore, the preset timing is defined in accordance with the temperature or the concentration that is detected by the detection device (the concentration sensor 18, or the temperature sensor 19 or 20) during the ultrafiltration treatment. Therefore, the dialysate can be delivered at an appropriate timing corresponding to the temperature or the concentration of the dialysate.

Furthermore, during the ultrafiltration treatment, the dialysate is heated by the heater 17 (the heating device) while the dialysate delivery is performed. Therefore, the dialysate to be supplied to the blood circuit in the substitution performed during the ultrafiltration treatment or in the blood return performed after the ultrafiltration treatment can have an appropriate temperature. In the first embodiment, during the ultrafiltration treatment with dialysate delivery, the dialysate is heated by the heater 17 provided to the dialysate introduction line L1. Alternatively, the dialysate may be heated by another heating device (for example, a heater provided on the outside of the dialysis device B, or the like).

Now, a blood purification apparatus according to a second embodiment of the present invention will be described.

The blood purification apparatus according to the second embodiment is applied to a hemodialysis apparatus, as with the case of the first embodiment, and chiefly includes, as illustrated in FIG. 1, a blood circuit in which an arterial blood circuit 2 and a venous blood circuit 3 are connected to a dialyzer 1 serving as a blood purification device; a dialysis device B including a duplex pump 7, an ultrafiltration pump 10, a dialysate introduction line L1, and a dialysate drain line L2; a dialysate supply line La; and a control device 21.

The second embodiment employs the same configuration as the first embodiment but is different from the first embodiment in the control process performed by the control device 21. The control process performed by the control device 21 according to the second embodiment will now be described with reference to the flow chart illustrated in FIG. 7 and to FIGS. 3 to 5.

First, the blood pump 4 is activated with the arterial puncture needle c and the venous puncture needle d being stuck in the patient, whereby the blood of the patient is removed and is taken into the blood circuit (S1). Subsequently, as illustrated in FIG. 4, the clamping devices (Vc and Vd) are closed while the clamping devices (Va and Vb) are opened on the side of the blood circuit. Furthermore, the electromagnetic valves (V1, V4, V5, and V7) are closed while the electromagnetic valves (V2, V3, V6, V8, and V9) are opened on the side of the dialysis device B. Furthermore, with the duplex pump 7 being active, the ultrafiltration pump 10 is activated while the blood pump 4 is kept active, whereby an ultrafiltration treatment with dialysate delivery is started (S2).

In the ultrafiltration treatment started in step S2, since the blood pump 4 is active, the blood extracorporeally circulates through the blood circuit. Furthermore, since the ultrafiltration pump 10 is activated, water is removed, by the effect of ultrafiltration, from the blood flowing in the hollow fiber membranes of the dialyzer 1 and is drained through the dialysate drain line L2. Meanwhile, since the duplex pump 7 is active, the dialysate is caused to flow through the dialysate introduction line L1, the bypass line L3, and the dialysate drain line L2. During the ultrafiltration treatment, dialysate delivery in the dialysate introduction line L1 is performed, and the heater 17 is activated to heat the dialysate.

Subsequently, if emergency fluid infusion is necessary, emergency fluid infusion is performed in step S3. In this emergency fluid infusion, as illustrated in FIG. 5, the clamping devices (Va and Vd) are closed while the clamping devices (Vb and Vc) are opened on the side of the blood circuit. Furthermore, the electromagnetic valves (V1, V2, V4, and V7) are closed while the electromagnetic valves (V3, V5, V6, V8, and V9) are opened on the side of the dialysis device B. Then, with the duplex pump 7 being active, the ultrafiltration pump 10 is stopped while the blood pump 4 is kept active, whereby the dialysate in the dialysate introduction line L1 is supplied to the blood circuit through the dialysate supply line La and is introduced as a substitution fluid into the body of the patient so as to counteract the reduction in blood pressure.

The above emergency fluid infusion in step S3 is performed after the ultrafiltration treatment with dialysate delivery performed in step S2. Therefore, the dialysate heated to a preset temperature by the heater 17 or having a preset concentration (composition) can be supplied to the blood circuit. Hence, no preparatory operations are necessary, and substitution can be performed by immediately supplying the dialysate in the dialysate introduction line L1 to the blood circuit during the ultrafiltration treatment. After substitution is performed as above, the ultrafiltration treatment with dialysate delivery illustrated in FIG. 4 (details have been described above) is restarted (S4).

Subsequently, if blood return after the treatment is to be performed, blood return is performed in step S5. In this blood return, as illustrated in FIG. 5, the clamping devices (Va and Vd) are closed while the clamping devices (Vb and Vc) are opened on the side of the blood circuit. Furthermore, the electromagnetic valves (V1, V2, V4, and V7) are closed while the electromagnetic valves (V3, V5, V6, V8, and V9) are opened on the side of the dialysis device B. Then, with the duplex pump 7 being active, the ultrafiltration pump 10 is stopped while the blood pump 4 is kept active, whereby the dialysate in the dialysate introduction line L1 is supplied to the blood circuit through the dialysate supply line La and is substituted for the blood in the blood circuit. Thus, the blood in the blood circuit can be returned to the patient.

The blood return in step S5 is performed after the ultrafiltration treatment with dialysate delivery performed in step S4. Therefore, the dialysate heated to a preset temperature by the heater 17 or having a preset concentration (composition) can be supplied to the blood circuit. Hence, no preparatory operations are necessary, and blood return can be performed by immediately supplying the dialysate in the dialysate introduction line L1 to the blood circuit after the ultrafiltration treatment. This is the end of the blood purification treatment.

According to the second embodiment, in the ultrafiltration treatment in which the ultrafiltration pump 10 is activated for ultrafiltration while the introduction of the dialysate into the dialyzer 1 is stopped, dialysate delivery is performed while the introduction of the dialysate into the dialyzer 1 is prevented. Therefore, with no preparatory operations, substitution can be performed by immediately supplying the dialysate in the dialysate introduction line L1 to the blood circuit during the ultrafiltration treatment, or blood return can be performed by immediately supplying the dialysate in the dialysate introduction line L1 to the blood circuit after the ultrafiltration treatment.

When the ultrafiltration treatment is performed by the blood purification apparatus according to the second embodiment, the ultrafiltration treatment with dialysate delivery alone is performed. Therefore, it is more assured that no preparatory operations are necessary than in the case of the first embodiment in which the ultrafiltration treatment is performed with the dialysate being delivered at a preset timing. In the second embodiment, the ultrafiltration treatment with dialysate delivery is performed with the activation of the duplex pump 7. Alternatively, dialysate delivery may be performed by another fluid delivering device.

Furthermore, during the ultrafiltration treatment, the dialysate is heated by the heater 17 (the heating device) while the dialysate delivery is performed. Therefore, the dialysate to be supplied to the blood circuit in the substitution performed during the ultrafiltration treatment or in the blood return performed after the ultrafiltration treatment can have an appropriate temperature. In the second embodiment, during the ultrafiltration treatment with dialysate delivery, the dialysate is heated by the heater 17 provided to the dialysate introduction line L1. Alternatively, the dialysate may be heated by another heating device (for example, a heater provided on the outside of the dialysis device B, or the like).

While the embodiments have been described above, the present invention is not limited thereto. For example, as long as the blood purification apparatus is capable of performing substitution or blood return by supplying the dialysate in the dialysate introduction line L1 to the blood circuit, the apparatus may perform substitution by supplying the dialysate in the dialysate introduction line L1 and perform blood return by introducing another substitution fluid such as a physiological saline solution. Alternatively, the apparatus may perform blood return by supplying the dialysate in the dialysate introduction line L1 and perform substitution by introducing another substitution fluid such as a physiological saline solution. In each of the above embodiments, the apparatus is controlled to perform both emergency fluid infusion and blood return. Alternatively, the apparatus may be controlled to perform only one of emergency fluid infusion and blood return. The control device 21 may be provided on the outside of the dialysis device B.

INDUSTRIAL APPLICABILITY

The present invention is also applicable to a blood purification apparatus having any other additional functions or the like, as long as the apparatus performs dialysate delivery while preventing the introduction of the dialysate into a blood purification device during the ultrafiltration treatment in which an ultrafiltration pump is activated for ultrafiltration while the introduction of the dialysate into a blood purification device is stopped.

REFERENCE SIGNS LIST 1 dialyzer (blood purification device)
2 arterial blood circuit
3 venous blood circuit
4 blood pump
5 arterial air-trap chamber
6 venous air-trap chamber
7 duplex pump
8, 9 filter
10 ultrafiltration pump
11 collection port
12 hydraulic-pressure-measuring sensor
13 venous-pressure sensor
14 pressurizing pump
15 degassing chamber
16 bubble detection sensor
17 heater (heating device)
18 concentration sensor (detection device)
19, 20 temperature sensor (detection device)
21 control device
L1 dialysate introduction line
L2 dialysate drain line
L7 atmosphere release line
La dialysate supply line
Lb overflow line
B dialysis device
a, b connector

The invention claimed is:

1. A blood purification apparatus comprising:
a blood circuit including an arterial blood circuit and a venous blood circuit through which blood of a patient extracorporeally circulates;
a blood purification device provided between the arterial blood circuit and the venous blood circuit and that purifies the blood flowing in the blood circuit;
a dialysate introduction line through which dialysate is introduced into the blood purification device, wherein the dialysate is provided at a preset timing;
a dialysate drain line through which drain liquid from the blood purification device is drained;
an ultrafiltration pump that removes water from the blood flowing in the blood circuit through the blood purification device,
a bypass line that bypasses the blood purification device and flows the dialysate in the dialysate introduction line into the dialysate drain line,
a fluid delivering device that delivers the dialysate in the dialysate introduction line to the blood purification apparatus;
a dialysate supply line that extends between and connects the dialysate introduction line and the blood circuit;
a closing device closing a flow route of the dialysate introduction line that extends between a connection to the bypass line and the blood purification device;
a supply line closing device in the dialysate supply line that closes the dialysate supply line; and
a control device that is a microprocessor that controls pumps, the closing device, and the supply line closing device, and further controls:
the fluid delivering device,
wherein while the ultrafiltration treatment is in progress, the control device checks the preset timing to determine whether the preset timing has been reached, and if the preset timing has not been reached, the ultrafiltration treatment is performed without delivery of the dialysate into the bypass line, and if the preset timing is reached, the ultrafiltration treatment is performed with delivery of the dialysate into the bypass line;
wherein the blood purification apparatus performs substitution or blood return by supplying the dialysate in the dialysate introduction line to the blood circuit,
wherein, in the ultrafiltration treatment in which the ultrafiltration pump is activated for ultrafiltration while the introduction of the dialysate through the dialysate introduction line into the blood purification device is stopped, dialysate delivery is performed while the introduction of the dialysate into the blood purification device is prevented; and
wherein the preset timing is a timing of an immediate response to a blood return or an emergency fluid infusion and at the blood return or the emergency fluid infusion the control device closes the closing device of the dialysate introduction line and opens the supply line closing device in the dialysate supply line so that dialysate from the dialysate supply line moves fluid to provide the blood return or the emergency fluid infusion.

2. The blood purification apparatus according to claim 1, wherein the preset timing is defined as a time based on a start time or an end time of the ultrafiltration treatment, or as a time when any condition for the ultrafiltration treatment is changed.

3. The blood purification apparatus according to claim 1, wherein the preset timing is defined in accordance with a parameter regarding a state of the patient or a state of the ultrafiltration treatment that is detected during the ultrafiltration treatment.

4. The blood purification apparatus according to claim 1, further comprising a detection device detecting a temperature or a concentration of the dialysate in the dialysate introduction line, wherein the preset timing is defined in accordance with the temperature or the concentration detected by the detection device during the ultrafiltration treatment.

5. The blood purification apparatus according to claim 1, further comprising a heating device heating the dialysate, wherein, during the ultrafiltration treatment, the dialysate is heated by the heating device while the dialysate delivery is performed.

6. The blood purification apparatus according to claim 4, further comprising a heating device heating the dialysate, wherein, during the ultrafiltration treatment, the dialysate is heated by the heating device while the dialysate delivery is performed.

7. The blood purification apparatus according to claim 4, wherein the concentration of the dialysate in the dialysate introduction line is monitored relative to a predetermined concentration.

8. The blood purification apparatus according to claim 7, wherein if the concentration of the dialysate detected by a concentration sensor is lower than or equal to the predetermined concentration, a duplex pump of the blood purification apparatus is activated.

9. The blood purification apparatus according to claim 1, further comprising a heater that heats the dialysate delivered by the dialysate introduction line.

10. The blood purification apparatus according to claim 9, further comprising a duplex pump that delivers the dialysate in the dialysate introduction line.

11. The blood purification apparatus according to claim 1, further comprising a duplex pump with a first temperature sensor located on a first side of the duplex pump and a second temperature sensor located on a second side of the duplex pump.

12. The blood purification apparatus according to claim 1, further comprising filters that purify the dialysate flowing through the dialysate introduction line.

13. The blood purification apparatus according to claim 12, wherein the filters are located between a duplex pump and an electromagnetic valve.

14. The blood purification apparatus according to claim 13, further comprising the bypass lines that are connected to the filters providing bypasses for the dialysate to be introduced into the dialysate drain line.

15. The blood purification apparatus according to claim 1, wherein the bypass line is two bypass lines that extend between the dialysate introduction line and the dialysate drain line.

16. The blood purification apparatus according to claim 1, wherein, after the ultrafiltration treatment, the control device performs emergency fluid infusion or blood return immediately.

17. The blood purification apparatus according to claim 1, wherein the control device controls the ultrafiltration pump during an ultrafiltration treatment to activate the ultrafiltration pump and perform ultrafiltration while stopping the dialysate that is introduced into the blood purification device.

18. The blood purification apparatus according to claim 1, wherein the control device controls the closing device during the ultrafiltration treatment to close the closing device so that the dialysate flows through the bypass line and is prevented from being introduced into the blood purification device while the fluid delivering device delivers the dialysate.

19. The blood purification apparatus according to claim 1, wherein the control device checks whether the preset timing has been reached.

* * * * *